United States Patent [19]
Honnick et al.

[11] Patent Number: 6,162,755
[45] Date of Patent: Dec. 19, 2000

[54] HETEROGENEOUS ORGANOTIN CATALYSTS

[75] Inventors: William D. Honnick, Chester, Pa.; Gerald H. Reifenberg, deceased, late of Mercer, N.J., by Gail H. Reifenberg, executrix; Kevin C. Cannon, Montgomery, Pa.

[73] Assignee: Elf Atochem North American, Inc., Philadelphia, Pa.

[21] Appl. No.: 09/428,346

[22] Filed: Oct. 27, 1999

Related U.S. Application Data

[62] Division of application No. 09/160,413, Sep. 25, 1998
[60] Provisional application No. 60/060,331, Sep. 29, 1997.

[51] Int. Cl.$^7$ .............................. B01J 31/00; B01J 31/12
[52] U.S. Cl. ........................ 502/152; 502/150; 502/154; 502/158
[58] Field of Search .................................. 502/150, 152, 502/154, 158

[56] References Cited

U.S. PATENT DOCUMENTS

| | | | |
|---|---|---|---|
| 4,954,472 | 9/1990 | Scott et al. | 502/152 |
| 5,436,357 | 7/1995 | Jiang et al. | 556/95 |
| 5,561,205 | 10/1996 | Jiang et al. | 526/240 |
| 5,834,393 | 11/1998 | Jacobsen et al. | 502/152 |

FOREIGN PATENT DOCUMENTS 31 19643   12/1982   Germany .

OTHER PUBLICATIONS

Mironov, V.F. et al., 44, 806 (1974) No Month Available.
Mironov, V.F. et al., 45, 2448 (1975) No Month Available.
Auner, N. et al., Allg. Chem. 500, 132 (1983) No Month Available.
Schumann, H. et al., Angew. Chem. Int. Ed. Engl., 20, 1043 (1981) No Month Available.
Schumann, H. et al., Organometal. Chem. 233, 281 (1982) No Month Available.
Matlin, S.A. et al., J. Chem. Soc., Chem. Commun., 798 (1984) No Month Available.
Mironov, V.F. et al., 42, 631 (1972) No Month Available.

*Primary Examiner*—Elizabeth D. Wood
*Attorney, Agent, or Firm*—Nicholas J. DeBenedictis; Stanley A. Marcus

[57] ABSTRACT

This invention provides: (a) new organotin functionalized silanes: (b) a solid prepared by chemically bonding organotin functionalized silanes to a solid inorganic support containing surface hydroxy groups: (c) a solid catalyst prepared from said supported organotin functionalized silane; (d) a process for conducting esterification or transesterification, and urethane, urea, silicone, and amino forming reaction utilizing said solid supported catalyst; (e) a process of separating the solid supported catalyst from the reaction products employing ligand—solid separation techniques; (f) reuse of the solid supported catalyst after being separated from the reaction products; (g) a continuous esterification or transesterification reaction or urethane, urea, silicone, or amino form.

10 Claims, No Drawings

HETEROGENEOUS ORGANOTIN CATALYSTS

This Application claims the benefit of U.S. Provisional Application 60/060,331 filed on Sep. 29, 1997. This application is a divisional of copending application application Ser. No. 09/160,413 filed on Sep. 25, 1998.

BACKGROUND OF THE INVENTION

This invention relates to tetravalent organotin compounds, particularly organotin functionalized silanes, a solid prepared by chemically bonding the organotin functionalized silane to an inorganic support containing surface hydroxy groups; a catalyst prepared from said supported organotin functionalized silane; a continuous or batch process for conducting esterification, or transesterification reactions, and urethane, urea, silicone, or amino forming reactions utilizing said solid supported catalyst and the reaction products of such continuous or batch processes involving the separation of the solid tin-containing catalyst from the liquid reaction products to yield tin catalyzed product containing very low levels of tin.

Homogeneous organotin compounds are known to be effective catalysts for esterification, transesterification, siloxane, and urethane forming reactions by those skilled in the art. However, separation of the homogeneous organotin catalysts from the reaction products is a major disadvantage which is frequently not possible or requires special treatment that usually destroys the catalyst. Homogeneous catalysts are in the same phase, usually liquid, as the reactants and reaction products. Heterogeneous catalysts are of a different phase than the reaction products.

Many types of heterogeneous catalysts are known and have a number of significant advantages over homogeneous catalysts such as ease of separation of the catalyst from the reaction products facilitating re-use of the catalysts and high mechanical and thermal stability over a wide range of processing conditions. Heterogeneous catalysts are sometimes not as selective as homogeneous catalysts. Supported metal complexes, metal complexes attached to the support by a chemical bond, are often as selective as their homogeneous counterparts.

There are two types of supports for heterogeneous catalysts, polymeric and inorganic. Polymer supports are popular because they are easily functionalized and have a flexible structure facilitating interactions between active catalyst sites and reactants. Polymer supports though have several significant disadvantages such as poor mechanical properties, limited thermal stability typically below 160° C., and a lack of physical rigidity over a wide range of processing conditions making control over the porosity and diffusional characteristics difficult.

Most known polymeric organotin compounds are not effective catalysts because of they do not possess the desired functionality for esterification; and transesterification reactopms, urethane, urea, silicone, and amino forming reactions or the fact that the tin tends to leach out too quickly from the polymer so that only a few reactions may be conducted. Jiang, et al in U.S. Pat. Nos. 5,436,357 and 5,561,205 have disclosed polymeric organotin compounds in which the organotin is attached to the polymer via a non-labile bond and found to be effective for transesterification reactions. However, the polymeric organotin compounds are limited to reactions temperatures in the range of 50 to 150° C. and thus are not expected to be effective for esterification reactions, typically carried out at temperatures exceeding 200° C. when homogeneous organotin catalysts are used.

Inorganic supports have a number of distinct advantages over polymer supports. They have a rigid structure which allows greater control over the porosity and diffusional characteristics of the support and are not affected by process conditions. The thermal stability is usually limited by the stability of the supported complex and not by the support itself. They also have high mechanical stability that prevents physical breakdown of the particle and the formation of "fines." Metal oxides are the most frequently used inorganic support owing to the fact that metal oxides contain surface hydroxyl groups which can be readily functionalized. Two modes of attachment are generally used for supporting complexes on the surface of metal oxides. The first is through the use of a metal complex that contains a labile ligand capable of reacting with the surface hydroxy groups to give a reaction product in which the metal center in the complex is directly bonded to the surface through an oxygen atom.

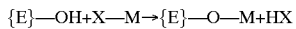

where
{E}—OH=metal oxide
M=metal center in the complex
X=labile ligand

Typically, the preferred mode of attachment of the metal complex is through the use of a functionalized silane that contains labile ligands on the silicon capable of reacting with the surface hydroxy groups of the metal oxide support such as

where
{E}—OH=metal oxide
X=MeO, EtO,Cl, . . .
Y=functional group

Leaching of the metal complex from the surface can be serious if there is any degree of dissociation of the metal under reaction conditions.

Most known organotin compounds are not suitable for preparing the heterogeneous catalysts of this invention because they either do not have the desired functionality for esterification, transesterification, and urethane, urea, silicone, and amino forming reactions, cannot be modified to contain such functionality, or do not form stable bonds with inorganic supports. The synthesis of several silylmethyltin trichlorides and bis(silylmethyl)tin dichlorides have been reported by Mironov, V. F., Stepina, E. M., and Shiryaev, E. M., Zh. Obshch Khim., 42 631 (1972); Mironov, V. F., Shiryaev, E. M., Yankov, V. V., Gladchenko, A. F. and Naumov, A. D., Zh. Obshch Khim., 44, 806 (1974); Mironov, V. F., Shiryaev, V. I., Stepina, E. M., Yankov, V. V., and Kochergin, V. P., Zh. Obshch Khim., 45, 2448 (1975), but do not disclose or suggest bonding these compounds to an inorganic support nor have they determined their effectiveness as catalysts. Similarly, Auner, N. and Grobe J., Z. Anorg. Allg. Chem. 500, 132 (1983) reported a number of 3-silylpropyltin trichlorides but do not disclose or suggest bonding these compounds to an inorganic support and have not determined their effectiveness as catalysts. Schumann, H and Pachaly, B., Angew. Chem. Int. Ed. Engl., 20, 1043 (1981); Schumann, H., and Pachaly, B., J. Organometal. Chem., 233, 281 (1982); Schumann, H., and Pachaly, B., Ger. Offen. 3116643, disclosed several organotin compounds that were supported on alumina and silica, however, they either do not contain the desired functionality for catalysis or there is a labile bond between the silicon and the tin. Matlin, S. A. and Gandharn, P. S., J. Chem. Soc., Chem. Commun., 798 (1984) reported the use of an organotin dimethoxide linked to the surface of silica that is effective as a hydride transfer catalyst for the reduction of ketones and aldehydes.

It is the object of this invention therefore, to produce organotin functionalized silanes wherein the organotin is linked to the silane by a stable ligand group(non-labile at both the tin and silicon ends), at least one of the ligands on the silane end of the molecule is labile and results in a stable silicon oxygen bond with the surface of the inorganic supports, and at least one of the ligands on the tin end of the molecule is a labile group.

Another object of this invention is to prepare a solid comprising an organotin functionalized silane on an inorganic support, which is useful in preparing a transesterification, esterification, or urethane forming catalyst.

A further object of this invention is to prepare a heterogeneous catalyst for transesterification, esterification, or urethane, urea, silicone, and amino forming reactions which has high selectivity, high activity and long catalyst life.

Yet another object of this invention is to provide a process for conducting transesterification, esterification, and urethane, urea, silicone, and amino forming reactions.

SUMMARY OF THE INVENTION

This invention provides four compositions of matter comprising: (1) an organotin silane; (2) a catalytically active functionalized organotin silane; (3) an organotin silane on a solid support comprising a metal oxide with surface hydroxy groups and, (4) catalytically active functionalized organotin silane on a solid support comprising a metal oxide with surface hydroxy groups. The formula for each is given in the detailed description.

Also provided is a solid supported organotin resulting from the reaction product of organotin silanes with solid metal oxides containing surface hydroxyl groups, such as glass, silica, mica, silica gel, alumina, aluminasiloxanes, kaolin, titania, zirconia and chromium oxide which have been discovered to be excellent heterogeneous catalysts for esterification or transesterification reactions or urethane, urea, silicone, and amino forming reactions.

A class of supported functionalized organotin silanes have been discovered to be excellent heterogeneous catalysts for esterification or transesterification reactions or urethane, urea, silicone, and amino forming reactions.

This invention also provides an improved process for conducting esterification or transesterification reactions or urethane, urea, silicone, or amino forming reactions comprising the steps of reacting non-solid phase reactants for an esterification or transesterification reaction or urethane, urea, silicone, or amino forming reaction in the presence of a catalytically effective amount of a solid supported organotin silane and separating from said solid catalyst, a non-solid phase containing the products of the reaction.

This invention further comprises the reuse of the heterogeneous catalyst after separating said solid catalyst from the reaction products.

Also provided is a continuous esterification or transesterification reaction or urethane, urea, silicone, or amino forming reactions comprising continuously reacting the reactants for an esterification or transesterification reaction or urethane, urea, silicone, or amino forming reaction in a reactor containing a catalytically effective amount of a solid supported organotin silane catalyst and continuously separating a non-solid phase containing the products of the reaction from said solid catalyst. Also provided is the reaction product of an esterification or transesterification reaction or urethane, urea, silicone, or amino forming reaction catalyzed with said solid supported organotin silanes catalyst and containing less than 100ppm tin after separating the non-solid phase containing the products of the reaction from said solid heterogeneous catalyst.

Improved synthesis of organotin silanes is also provided involving the reaction of 1,1-dihalosilacycloalkane (e.g. 1,1-diclorosilacyclobutane) with tin tetrachloride to give the corresponding 3-silapropyltin trichloride compounds in the presence of a catalytically effective amount of a Lewis acid such as aluminum trichloride to yield a mixture of 3-(trihalorosilyl)propyl tin trihalide, such as 3-(trichlorosilyl)propyl tin trichloride and di-(3-trihalosilyl) propyl tin dihalide such as di-3-(trichlorosilyl)propyl tin dichloride. Novel syntheses involving ring opening is provided for producing organotin functional silanes in which a Lewis acid catalyst is used in the reaction of a dihalosilacycloalkane such as 1,1-dichlorosilacyclobutane with an organotin halide, such as butyltin trichloride to open up the silacyclobutane ring and yield 3-(trihalosilyl)propyl organotin halides such as 3-(trichlorosilyl)propyl butyltin dichloride. If the chloride functionality in the dichlorosilyacyclobutane is replaced with dialkoxy or diaryloxy functional groups, then the need for a Lewis acid catalyst is eliminated in the ring opening reaction to produce organotin silanes.

DETAILED DESCRIPTION OF THE INVENTION

This invention provides four compositions of matter comprising: (1) an organotin silane; (2) a catalytically active functionalized organotin silane; (3) an organotin silane on a solid support comprising a metal oxide with surface hydroxy groups and, (4) a catalytically active functionalized organotin silane on a solid support comprising a metal oxide with surface hydroxy groups.

The formula (hereinafter referred to as Formula 1) for the organotin silane is

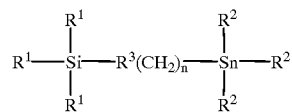

wherein: each $R^1$ is independently selected from the group consisting of F, Cl, Br, I, OR, and R, where R is substituted or unsubstituted $C_1$ to $C_{12}$ alkyl, $C_5$ to $C_{12}$ cycloalkyl, or aryl, provided at least one value of $R^1$ is selected from among F, Cl, Br, I, and OR each $R^2$ is independently selected from $R^1$, benzyl, vinyl, allyl, hydride, and

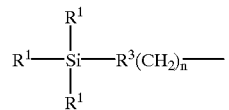

provided at least one value of $R^2$ is F, Cl, Br, I, or OR $R^3$ is $(CH_2)_m$, aryl or cycloalkyl, m=0 to 17, n=1 to 18, sum of n plus m=1 to 18 except when $R^3$ is aryl or cycloalkyl then n =at least 2, except, when $R^3=(CH_2)_m$, n=1, m=0, at least one value of $R^1$ is Cl, methoxy or ethoxy, or when $R^2$ is

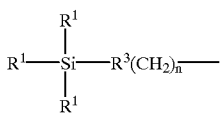

then, all of the values of $R^2$ cannot be selected from Cl and I; and, except also, when $R^3=(CH_2)_m$, the sum of n plus m=2, 4, 5 or 6, all values of $R^1$ are R with R being aryl or $C_1$ to $C_{12}$ alkyl, one value of $R^2$ is Cl, aryl or hydride; then, all remaining values for $R^2$ cannot be selected from $C_1$ to $C_{12}$ alkyl, $C_7$ to $C_{18}$ cycloalkyl or aryl; and, except also, when $R^3=(CH_2)_m$, the sum of n plus m=3, at least one value of $R^1$ is Cl, all other values of $R^1$ are selected from Cl, $CH_3$, vinyl, or phenyl and one value of $R^2$ is Cl,; then, all remaining values of $R^2$ cannot be selected from among Cl and methyl; and except also, when $R^3=(CH_2)_m$, the sum of n plus m=4, all values of $R^1$ are Cl, and two values for $R^2$ are Cl then the remaining value for $R^2$ cannot be butyl.

The formula (hereinafter referred to as Formula 2) for the catalytically active functionalized organotin silane:

comprising a compound of the formula:

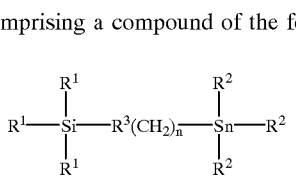

wherein: each $R^1$ is independently selected from the group consisting of F, Cl, Br, I, OR, and R, where R is substituted or unsubstituted $C_1$ to $C_{18}$ alkyl, $C_5$ to $C_{12}$ cycloalkyl, or aryl, provided at least one value of $R^1$ is selected from among F, Cl, Br, I, and OR; each $R^2$ is independently selected from $R^1$, benzyl, vinyl, allyl, hydride, hydroxide, sulfide, sulfate, carbonate, phosphate, phosphite, phosphonate, sulfonate, mercapto, a residue of a mercapto acid, mercapto alcohol, or mercaptoesters, carboxylates substituted or unsubstituted of $C_1$ to about $C_{20}$, and

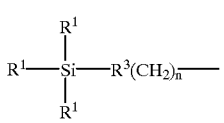

provided at least one value of $R^2$ is selected from among hydroxide, sulfide, sulfate, carbonate, phosphate, phosphite, phosphonate, sulfonate, mercapto, a residue of a mercapto acid, mercapto alcohol, or mercaptoesters, and carboxylates substituted or unsubstituted of $C_1$ to about $C_{20}$; $R^3$ is $(CH_2)_m$, aryl or cycloalkyl, m=0 to 17, n=1 to 18, sum of n plus m=1 to 18 except when $R^3$ is aryl or cycloalkyl then n=at least 2, The formula (hereinafter referred to as Formula 3) for the organotin silane on solid support comprising a metal oxide with surface hydroxy groups is:

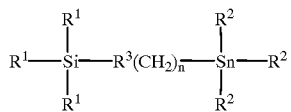

wherein: each $R^1$ is independently selected from the group consisting of F, Cl, Br, I, M—O—, OR, R, where R is substituted or unsubstituted $C_1$ to $C_{18}$ alkyl, $C_5$ to $C_{12}$ cycloalkyl, or aryl, provided at least one value of $R^1$ is M—O—; each $R^2$ is independently selected from $R^1$, benzyl, vinyl, allyl, hydride, and;

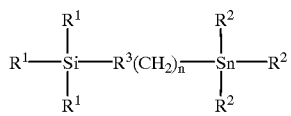

$R^3$ is $(CH_2)_m$, aryl or cycloalkyl m=0 to 17, n=1 to 18, sum of n plus m=1 to 18 except when $R^3$ is aryl or cycloalkyl then n=at least 2, and M—O— is the metal oxide component of the solid support; except, when $R^3=(CH_2)_m$, the sum of n plus m=2, 4, 5 or 6, all values of $R^1$ are R with R being aryl or $C_1$ to $C_{12}$ alkyl, one value of $R^2$ is Cl aryl or hydride; then, all remaining values for $R^2$ cannot be selected from $C_1$ to $C_{12}$ alkyl, $C_7$ to $C_{18}$ cycloalkyl or aryl; and except also, when $R^3=(CH_2)_m$, the sum of n plus m=4, all values of $R^1$ are Cl, and two values for $R^2$ are Cl or when all values of $R^1$ are methoxy and two values for $R^2$ are methoxy, then the remaining value for $R^2$ cannot be butyl.

The formula (hereinafter referred to as Formula 4) for the catalytically active, functionally organotin silane on a solid support comprising a metal oxide with surface hydroxy groups is:

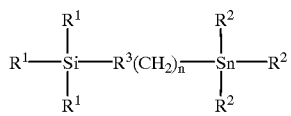

wherein:
each $R^1$ is independently selected from the group consisting of F, Cl, Br, I, M—O—, OR, R, where R is substituted or unsubstituted $C_1$ to $C_{18}$ alkyl, $C_5$ to $C_{12}$ cycloalkyl, or aryl, provided at least one value of $R^1$ is M—O—; each $R^2$ is independently selected from $R^1$, benzyl, vinyl, allyl, hydride, hydroxide, sulfide, sulfate, carbonate, phosphate, phosphite, phosphonate, sulfonate, mercapto, a residue of a mercapto acid, mercapto alcohol, or mercaptoesters, carboxylates substituted or unsubstituted of $C_1$ to about $C_{20}$. and

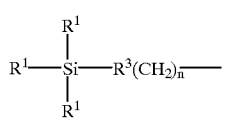

provided at least one $R^2$ is selected from among hydroxide, sulfide, sulfate, carbonate, phosphate, phosphite, phosphonate sulfonate, mercapto, a residue of a mercapto acid, mercapto alcohol, or mercaptoesters, and carboxylates substituted or unsubstituted of $C_1$ to about $C_{20}$.; $R^3$ is $(CH_2)_m$, aryl or cycloalkyl; m=0 to 17, n=1 to 18, sum of n plus m=1 to 18 except when $R^3$ is aryl or cycloalkyl then n=at least 2; and M—O— is the metal oxide component of the solid support.

The synthesis of the organotin silanes and chemically bonding them to a solid support comprising a metal oxide with surface hydroxy groups is disclosed hereinafter and shown in the examples at least for the preferred embodiments.

A heterogeneous organotin silane catalyst is provided comprising, the organotinsilane of Formulas 3 and 4 are made by chemically bonding (supporting) an organotin silane of Formula 1 or 2 onto a solid metal oxide containing surface hydroxy groups via at least one metal—O—Si bond. Preferably is the functionalized heterogeneous organotin silane of Formula 4. The compounds of Formula 4 can be synthesized by either by bonding the compound of Formula 2 onto the solid support or by bonding the compound of Formula 1 onto the support and then improving the catalytic functionality by replacing at least one of the labile groups on the tin of Formula 1 with the sunstituent groups for $R^2$ contained in the Formula 2 verses Formula 1.

Improving the catalytic functionality of Formula 1 or Formula 3 can be increased by converting them to the compounds of Formula 2 and Formula 4 respectively. This is accomplished when the labile group on the tin is replaced by reacting it with a reagent selected from the group consisting of alkali and alkaline hydroxides, oxides, carbonates, bicarbonates, phospates, phosphinates, sulfates, organic acid salts, sulfonates, alcohols, phenols, and inorganic or organic acids. This results in a class of supported functionalized organotin silanes that have been discovered to be excellent heterogeneous catalysts for esterification or transesterification reactions or urethane, urea, silicone, and amino forming reactions. For catalytic properties, the key requirement for this functional group is that it result in a labile bond with the tin under reactions conditions typically used for esterification or transesterification reactions or urethane, urea, silicone, and amino forming reactions. The catalytically active groups on the tin include F, Cl, Br, I, M—O—, OR, benzyl, vinyl, allyl, hydride, hydroxide, sulfide, sulfate, carbonate, phosphate, phosphite, phosphonate, sulfonate, mercapto, a residue of a mercapto acid, mercapto alcohol, or mercaptoesters, carboxylates substituted or unsubstituted of $C_1$ to about $C_{20}$. However the preferred groups are Cl, Or, oxide, hydroxide, sulfonate, or carboxylates substituted or unsubstituted of $C_1$ to about $C_{20}$.

The supported organotin silanes compounds of Formula 3 and Formula 4 have been discovered to be excellent heterogeneous catalysts for esterification or transesterification reactions or urethane, urea, silicone, and amino forming reactions.

Organotin silanes of the Formula 1 in which m equals 0 and n plus m equals 3 can be produced utilizing a novel ring opening reaction of silyacyclobutanes with tin halides followed by subsequent functionalizing with the above stated reactions. The only reported examples of such a ring opening reaction were limited to the reactions of 1,1-dichloro and 1,1-dimethylsilacylobutane with tin tetrachloride to give the corresponding 3-silylpropyltin trichloride compounds. Although the reaction of 1,1 -dichlorosilacyclobutane with tin tetrachloride is reported by Auner and Grobe, it was found that this reaction does not occur in significant conversion of the silacyclobutane to give the expected organotin silane. Surprisingly it was found that by adding a small amount of a suitable Lewis acid catalyst, such as aluminum trichloride, the reaction occurred to give a mixture of 3-(trichlorosilyl)propyl tin trichloride and di-3-(trichlorosilyl)propyl tin dichloride. Using a Lewis acid catalyst, 1,1-dichlorosilacyclobutane reacts with organotin halides, such as butyltin trichloride to open up the silacyclobutane ring and give 3-(trichlorosilyl)propyl butyltin dichloride.

It has been discovered that the reaction of tin tetrahalides and organotin halides with 1,1-dialkoxysilacyclobutanes proceed without the need for a catalyst.

An improved esterification or transesterification reaction or urethane, urea, silicone, or amino forming reaction is provided of the type comprising reacting non-solid phase reactants for an esterification or transesterification reaction or urethane, urea, silicone, or amino forming reaction wherein the improvement comprises the steps of reacting said non-solid phase reactants in the presence of a catalytically effective amount of a solid supported organotin silane catalyst of the present invention (Formula 3 or Formula 4) , and separating from said solid catalyst a non-solid phase containing the products of the reaction. This results in a reaction product that has been catalyzed with a tin containing catalyst and contains very little tin after the phase separation operation in which the solid catalyst is separated from the non-solid reaction product. Phase separation operations such as liquid-solid and gaseous-solid separation operations are well known unit operations in chemical engineering and practiced commercially. Filteration, centrifugation, settling, and entrainment are but a few known unit operations that use phase differences to effect a separation of materials. In addition, separation can be effectuated when the solid catalyst is in a reactor such as a packed bed or column into which non-solid reactants are added and non-solid reaction products are removed, thereby effectuating the separation of non-solid reaction products from the solid catalyst. A reactor containing solid catalyst of the present invention can be used to continuously conduct esterification or transesterification reaction or a urethane, urea, silicone, or amino forming reaction. This is accomplished by continuously adding non-solid reactants to a reactor containing the catalyst and continuously removing from the reactor a stream containing non-solid reaction products.

Whether practiced continuously or batchwise, after separation of the solid catalyst from reaction products, the reaction products are surprisingly low in tin impurities, generally less than 100 ppm and can be less than 10 ppm. This purity is accomplished by a simple phase separation in which the solid (heterogeneous) catalyst is separated from the non-solid, usually liquid, reaction products. Also, this purity is due to the fact that the tin catalyst is not readily extractable from it's solid support due to the strong bond between the support and the organotin silane achieved by the M—O—Si bond. Reducing or eliminating tin impurities is an important consideration when the reaction product of an esterification or transesterification reaction or urethane, urea, silicone, or aminos forming reaction will be used in food contact applications, e.g. containers, or for human ingestion such as pharmaceutical products.

The heterogeneous organotin silane catalyst is a solid supported organotin silane resulting from the reaction product of an organotin silane of Formula 1 or Formula 2 with a solid support having a metal oxide containing hydroxyl groups on the surface of the solid support. Examples of suitable metal oxide materials are glass, such as silica, mica, silica gel, alumina, aluminasiloxanes, kaolin, titania, zirconia and chromium oxide. Suitable supports can be solid, hollow or porous particles of such materials or composites having such materials on the surface of the particle. The present invention is independent of the shape and size of the solid support. While beads are a common shape for supports, any convenient shape and size may be utilized and selected for practicing the present invention based on considerations such as a good surface area to weight ratio and/or ease of separation of the solid catalyst from the non-solid reaction products.

One or more of the labile groups (i.e. F, Cl, Br, I, or OR) on the tin of the supported catalyst defined by Formula 1 and Formula 3 is preferable replaced with a group having improved catalytic properties. This can be accomplished by reacting the organotin silane, either before or after in is bonded to the support (after is preferred), with a wide variety of reagents such as alkali and alkaline hydroxides, oxides, carbonates, bicarbonates, sulfates, phosphate, phosphite, phosphinate, organic acid salts, sulfonates, and by reaction with alcohols, phenols, acids (both inorganic and organic), and other reagents known to those skilled in the art for substituting the halide functionality on an organotin halide. This results in the labile group (i.e. F, Cl, Br, I, or OR) on the tin being replaced with a functional group such as oxide, hydroxide, carboxylate, bicarboxylate, sulfate, organic salt, sulfonate, phenol, inorganic or organic acids, mercaptide, phosphate, phosphite, phosphinate and carbonate. Although the organotin silane with the halide labile group on the tin is catalytically active, preferably, the halide group on the organotin silane is replaced with another functional group by the reaction discussed above. Adding the improved catalytical functionality to the organotin silane after it has been reacted with the metal oxide containing support is preferred because it avoids the labile group or groups on the silane from being also replaced with the functional group. The labile group of groups on the silane are better utilized as the site for forming the Me—O—Si bond for chemically attaching the organotin silane to the support.

A novel, ring opening, synthesis has been discovered for a subgroup of the organotin silanes of Formula 1. The subgroup has the formula:

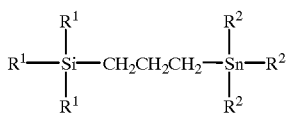

wherein $R^1$ and $R^2$ have the same values as in Formula 1. The synthesis can be best described by the following general reaction scheme using Cl for $R^1$ and $R^2$ and $AlCl_3$ for the Lewis Acid catalyst. It should be understood that $R^1$, and $R^2$ can have any of the values given in Formula 1 and any Lewis Acid catalyst can be used.

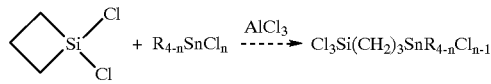

Where n = 1 to 4

In this general reaction scheme the Lewis acid (aluminum trichloride) will catalyze the reaction of any organotin halide with 1,1-dihalosilacyclobutane and in which R can be alkyl or aryl (unsubstituted or substituted), alkylene or the silyl group itself $X_3Si(CH_2)_3$—.

The reactions will give a product or a mixture of products depending on the value of n in the general reaction scheme. These are shown for the series of reaction for each value of n:

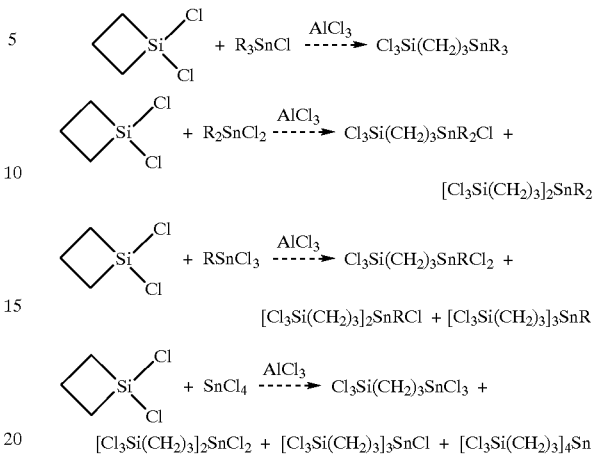

Furthermore, $AlCl_3$ is well known to those skilled in the art as an effective catalyst for the redistribution reaction of organotins. There are potentially other species that may be formed by the scrambling or R, $Cl_3Si(CH_2)_3$—, and Cl groups on the tin which exist in equilibrium. Accordingly, the product is better described as a reaction product rather than by the above structural formula. The relative amounts of the reaction products in the mixture will vary depending on the mole ratio of the reactants, that is the mole ratio of the 1,1-dichlorosilacyclobutane reacted with the halide.

Also discovered is another synthesis not requiring a Lewis acid catalyst involving the reaction of 1,1-dialkoxysilacyclobutane, such as 1,1-dimethoxysilacyclobutane, with $R_{4-n}SnCl_n$. The reactions for different values of $R_{4-n}$ showing the mixtures of reaction products the above, except that the chlorides on the silicon are replaced with RO— groups, and there is no need for Lewis acid catalyst.

The reactivity of the tin halide decreases with an increase in the organic functionality on the tin, i.e. the reactivity decreases in the order $SnCl_4 > RSnCl_3 > R_2SnCl_2$, and $R_3SnCl$. This is particularly true for the uncatalyzed reactions.

Synthesis of Type A Organotin Functionalized Silanes

Comparative Example A Attempted reaction of 1,1-dichlorosilacyclobutane with Tin Tetrachloride 1,1-Dichlorosilacyclobutane (7.14 grams) and tin tetrachloride (13.70 grams) were transferred into a tube under nitrogen. The tube was sealed and placed in oil bath and held at 132° C. for 18.5 hours. Analysis of the reaction mixture by $^{119}Sn$ and 29Si NMR indicated virtually no reaction had occurred.

Example 1 $AlCl_3$ Catalyzed Reaction of 1,1-dichlorosilacyclobutane with Tin Tetrachloride 1,1-Dichlorosilacyclobutane (6.77 grams, 0.048 mole), tin tetrachloride (13.58 gram, 0.051 mole) and aluminum trichloride (0.44 gram, 0.0033 mole) were transferred into a tube under nitrogen. The tube was sealed and placed into an oil bath and held at 133° C. for 24 hours. $^{29}$ Si NMR showed 100% conversion of the 1,1-Dichlorosilacyclobutane. $^{119}$Sn NMR showed 21.1 mole % $Cl_3Si(CH_2)_3SnCl_3$, 25.8 mole % $[Cl_3Si(CH_2)_3]_2SnCl_2$, and 53.1 mole % tin tetrachloride.

Example 2 AlCl$_3$ catalyzed reaction of 1,1-Dichlorosilacyclobutane with Tin Tetrachloride 1,1-Dichlorosilacyclobutane (28.54 grams, 0.202 mole), tin tetrachloride (26.62 grams, 0.102 mole) and aluminum trichloride (1.00 grams, 0.0075 mole) were transferred into a 100 ml flask under nitrogen. The mixture was heated at reflux for 18 hours. $^{119}$Sn nmr showed that all the tin tetrachloride had been converted to 95.1 mole % [Cl$_3$Si(CH$_2$)$_3$]$_2$SnCl$_2$ and 4.1 mole % Cl$_3$Si(CH$_2$)$_3$SnCl$_3$.

Example 3 AlCl$_3$ catalyzed reaction of 1,1-Dichlorosilacylubutane with Butyltin Trichloride 1,1-Dichlorosilacyclobutane (12.79 grams, 0.907 mole), butyltin trichloride (25.59 grams, 0.907 mole), and aluminum trichloride (0.70 grams, 0.0052 mole) were transferred into a 100 ml flask under nitrogen. The mixture was heated and refluxed for 25 hours. GC-MS analysis showed 46.8 area % [Cl$_3$Si(CH$_2$)$_3$Sn(Bu)Cl$_2$, and 34.4 area % [Cl$_3$Si(CH$_2$)$_3$]$_2$Sn(Bu)Cl.

Example 4 Reaction of 1,1-Dimethoxysilacyclobutane with Tin Tetrachloride 30.0 grams (0.227 mole) of 1,1-dimethoxysilacyclobutane, 76.0 grams (0.294 mole) of tin tetrachloride, and 170 ml of toluene were transferred into a flask under nitrogen and stirred for 18 hours at 25° C. The reaction mixture was then heated and refluxed for 6 hours. The reaction product, represented by the formula (MeO)$_2$ClSi(CH$_2$)$_3$SnCl$_3$ was isolated by removing the solvent and then vacuum distilled at 123–126° C. at 1 torr. Elemental analysis gave 30.9% Sn and 7.76% Si.

Example 5 Reaction of 1,1-Dimethoxysilacyclobutane with Butyltin Trichloride 30.0 grams (0.227 mole) of 1,1-dimethoxysilacyclobutane, 64.1 grams (0.227 mole) of butyltin trichloride were transferred into a flask under nitrogen and stirred at 80° C. for 30 hours. The reaction product, represented by the formula (MeO)$_2$ClSi(CH$_2$)$_3$Sn(Bu)Cl$_2$ was vacuum distilled at 160° C. at 1 torr. Elemental analysis gave 24.0% Sn and 6.55% Si.

Synthesis of Type B Organotin Functionalized Silanes

Example 6 Reaction of (MeO)$_3$SiCH$_2$Cl With SnCl$_2$ 20.0 grams of (MeO)$_3$SiCH$_2$Cl, 11.11 grams of SnCl$_2$, and 1.30 grams of n-Pr$_4$NCl, were transferred into a flask under nitrogen and heated at 154° C. for 3 hours. The reaction mixture was filtered and then vacuum distilled at 88–90° C. and 2 torr. Elemental analysis of the isolated product gave 32.4% Sn, 7.61% Si, and 29.2% Cl which is represented by the formula (MeO)$_3$SiCH$_2$SnCl$_3$.

Bonding of Organotin on Silica

Drying of Silica (Preparation of Support)

98.0 grams of silica gel, Davisil grade 646 available from W. R. Grace, was placed in a 1 liter flask and heated to 95° C. at 1.8 torr for 5 hours to produce silica gel for use in the examples.

Comparative Example B Attempted Support of Monobutyltin Trichloride on Silica 25 grams of dried silica was transferred to a 250 ml flask under dry nitrogen. 75 ml of toluene was added via syringe to the reaction flask followed by addition of 10.4 ml (6.14 grams) of monobutyltin trichloride. The mixture was heated and allowed to reflux under nitrogen for 18 hours. The volatiles were then removed under vacuum to give a solid. 8.52 grams of the solid was Soxhlet extracted with methanol for 18.5 hours. The wet solid was then dried under vacuum. Elemental analysis for tin gave 0.13% Sn. The calculated percent tin assuming complete reaction of the monobutyltin trichloride to give a product as represented by {Si}—O—Sn(Bu)Cl$_2$ is 8.5% Sn.

Comparative Example C Attempted Support of Tin Tetrachloride on Silica 11.0 grams of dried silica and 7.16 grams of tin tetrachloride were transferred to a reaction flask under nitrogen and 30 ml of toluene added. The mixture was refluxed for 5 hours, cooled to room temperature, and filtered. The solid was Soxhlet extracted with methanol for 20 hours and dried under vacuum to give 8.82 grams of a solid. The elemental analysis of the reaction product gave 0.74% Sn.

Example 7 Bonding of Mixture of [Cl$_3$Si(CH$_2$)$_3$]$_2$SnCl$_2$ on Silica 6.00 grams of dried silica, about 30 ml of toluene and 4.99 grams of from [Cl$_3$Si(CH$_2$)$_3$]$_2$SnCl$_2$ Example 3 were transferred into a flask under nitrogen and refluxed for 5 hours. The reaction mixture was cooled and filtered, and the solids Soxhlet extracted with methanol for 24 hours. The solids were then dried under vacuum. Elemental analysis gave 5.5% Sn.

Example 8 Bonding of (MeO)$_2$ClSi(CH$_2$)$_3$SnCl$_3$ on Silica 101.6 grams of dried silica, 259.5 grams of toluene and 16.62 grams of (MeO)$_2$ClSi(CH$_2$)$_3$SnCl$_3$ from Example 4 were transferred into a flask under nitrogen and refluxed for 5 hours. The reaction mixture was cooled and filtered, and the solids Soxhlet extracted with methanol for 30 hours. The solids were then dried under vacuum. Elemental analysis gave 3.98% Sn and 2.12% Cl.

Example 9 Bonding of (MeO)$_2$ClSi(CH$_2$)$_3$Sn(Bu)Cl$_2$ 61.8 grams of dried silica, 158.8 grams of toluene and 17.9 grams of (MeO)$_2$ClSi(CH$_2$)$_3$Sn(Bu)Cl$_2$ from Example 5 were transferred into a flask under nitrogen and refluxed for 5 hours. The reaction mixture was cooled and filtered, and the solids Soxhlet extracted with methanol for 24 hours. The solids were then dried under vacuum. Elemental analysis gave 6.02% Sn and 3.23% Cl.

Example 10 Bonding of (MeO)$_3$SiCH$_2$SnCl$_3$ on Silica 4.04 grams of (MeO)$_3$SiCH$_2$SnCl$_3$ from Example 6, 26.92 grams of dried silica, and 68.66 grams of toluene were transferred to a flask under nitrogen and refluxed for 5 hours. The reaction mixture was cooled and filtered, and the solids Soxhlet extracted with methanol for 24 hours. The solids were then dried under vacuum. Elemental analysis gave 3.83% Sn and 1.91% Cl.

Example 11 Reaction of Silica Bonded (MeO)$_2$ClSi(CH$_2$)$_3$SnCl$_3$ with Sodium Acetate 5.56 grams of silica bound (MeO)$_2$ClSi(CH$_2$)$_3$SnCl$_3$ from Example 8, 3.60 grams of sodium acetatetrihydrate, and 60 ml of methanol were transferred into a flask and heated at reflux for 2 hours. The solids were filtered and then Sohxlet extracted with methanol for 20 hours. The extracted solids were dried under vacuum. Elemental analysis gave 4.11% Sn and 0.04% Cl.

Esterification Reactions

General Procedure: 111.09 grams of phthalic anhydride (0.75 mole), 234.41 grams of 2-ethyl hexanol (1.80 mole), and the appropriate amount of catalyst added to give 116.1 mg of Sn contained in the catalyst per 100 grams of phthalic anhydride were transferred into a 1 liter flask fitted with a Dean and Stark separator. The reaction flask was purged with nitrogen for 15 minutes and then the temperature of the reaction mixture increased to 220° C. The reaction mixture begins refluxing at 175° C. and reaction times are taken from the time at which the reaction mixture reaches 175° C. The amount of unreacted acid at the end of the reaction is expressed in terms of Acid Number (mg of KOH per gram of sample).

Example 12 Esterification Reactions using Heterogeneous Organotin Catalysts

| Catalyst | Acid Number | Reaction Time (hrs) |
|---|---|---|
| Example 7 | 0.19 | 7 |
| Example 8 | 0.13 | 6 |
| Example 9 | 0.14 | 6 |
| Example 10 | 0.09 | 4 |
| Example 11 | 0.11 | 5 |

Example 13 Esterification Reactions - Catalyst Recycle

Esterification reactions were carried out as described as in the General Procedure. At the end of each reaction, liquid reaction product was separated from the solid heterogeneous organotin catalyst by the simple liquid-solid separation operation of filtering. This was accomplished by removing the reaction product from the reaction flask through a filter tube inserted into to reaction flask, leaving the catalyst in the flask along with a small amount of reaction product. Phthalic anhydride and 2-ethyl hexanol were then added to the flask and another esterification reaction carried out with the same catalyst that remained in the flask. The reuse of the catalyst with additional reactants was repeated up to six times with monitoring of the acid number and time to determine how long it took for the reaction to reach completion. The results are given in the following table:

| Catalyst | Example 7 | Example 9 |
|---|---|---|
| Initial | 0.8 (6) | 0.09 (4) |
| 1 | 0.08 (5.5) | 0.05 (4.5) |
| 2 | 0.04 (5.5) | 0.11 (5) |
| 3 | 0.15 (5.5) | 0.17 (6) |
| 4 | 3.3 (6) | 0.24 (6) |
| 5 | 0.11 (6) | 2.8 (6) |
| 6 | 0.14 (6) | |

Acid number with reaction time in hours given in parentheses

What is claimed is:

1. An organotin silane chemically bonded to a solid metal oxide through an oxygen bridge and capable of catalyzing an esterification or transesterification reaction or a urethane, urea, silicone, or amino forming reaction comprising the reaction product of:

(a) a solid support containing a metal oxide with surface hydroxy groups, and (b) one or more an organotin silanes of the formula

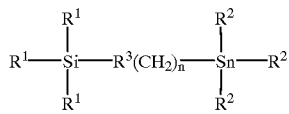

wherein:

each $R^1$ is independently selected from the group consisting of F, Cl, Br, I, OR, and R, where R is substituted or unsubstituted $C_1$ to $C_{18}$ alkyl, $C_5$ to $C_{12}$ cycloalkyl, or aryl, provided at least one value of $R^1$ is selected from among F, Cl, Br, I, and OR;

each $R^2$ is independently selected from $R^1$, benzyl, vinyl, allyl, hydride, and OR; where R is alkyl or

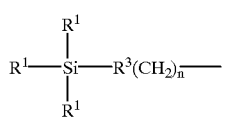

provided at least one value of $R^2$ is F, Cl, Br, I, or OR;

$R^3$ is $(CH_2)_m$, aryl or cycloalkyl, m=0 to 17, n=1 to 18, sum of n plus m=1 to 18 except when $R^3$ is aryl or cycloalkyl then n=at least 2, except, when $R^3=(CH_2)_m$, the sum of n plus m=2, 4, 5 or 6, all values of $R^1$ are R with R being aryl or $C_1$ to $C_{12}$ alkyl, and one value of $R^2$ is Cl, aryl or hydride;

then, all remaining values for $R^2$ cannot be selected from $C_1$ to $C_{12}$ alkyl, $C_7$ to $C_{18}$ cycloalkyl or aryl; and with the further proviso that, when $R^3=(CH_2)_m$, the sum of n plus m=4, all values of $R^1$ are Cl, and two values for $R^2$ are Cl, then the remaining value for $R^2$ cannot be butyl.

2. An organotin silane chemically bonded to a solid metal oxide through an oxygen bridge and capable of catalyzing esterification or transesterification reaction or a urethane, urea, silicone, or amino forming reaction comprising a compound of the formula:

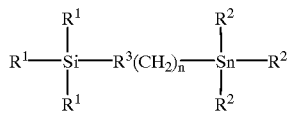

wherein:

each $R^1$ is independently selected from the group consisting of F, Cl, Br, I, M—O—, OR, and R, where R is substituted or unsubstituted $C_1$ to $C_{18}$alkyl, $C_5$ to $C_{12}$ cycloalkyl, or aryl, provided at least one value of $R^1$ is M—O—;

each $R^2$ is independently selected from $R^1$, benzyl, vinyl, allyl, hydride, and OR; where R is alkyl or

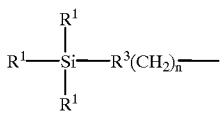

$R^3$ is $(CH_2)_m$, aryl or cycloalkyl;

m=0 to 17, n=1 to 18, sum of n plus m=1 to 18 except when $R^3$ is aryl or cycloalkyl then n=at least 2, and M—O— is the metal oxide component of the solid support;

except, when $R^3=(CH_2)_m$, the sum of n plus m=2, 4, 5 or 6, all values of $R^1$ are R with R being aryl or $C_1$ to $C_{12}$ alkyl, and one value of $R^2$ is Cl aryl or hydride;

then, all remaining values for $R^2$ cannot be selected from $C_1$ to $C_{12}$ alkyl, $C_7$ to $C_{18}$ cycloalkyl or aryl; and with the further proviso that when $R^3=(CH_2)_m$, the sum of n plus m=4, all values of $R^1$ are Cl, and two values for $R^2$ are Cl or when all values of $R^1$ are methoxy and two values for $R^2$ are methoxy, then the remaining value for $R^2$ cannot be butyl.

3. A catalytically active organotin silane chemically bonded to a solid metal oxide through an oxygen bridge and capable of catalyzing an esterification or transesterification reaction or a urethane, urea, silicone, or amino forming reactions comprising a compound of the formula:

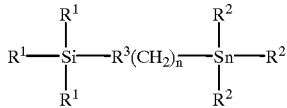

wherein:
each $R^1$ is independently selected from the group consisting of F, Cl, Br, I, M—O—, OR, and R, where R is substituted or unsubstituted $C_1$ to $C_{18}$alkyl, $C_5$ to $C_{12}$ cycloalkyl, or aryl, provided at least one value of $R^1$ is M—O—;
each $R^2$ is independently selected from $R^1$, benzyl, vinyl, allyl, hydride, hydroxide, sulfide, sulfate, carbonate, phosphate, phosphite, phosphonate, sulfonate, mercapto, mercapto alcohol, or mercaptoesters, carboxylates substituted or unsubstituted of $C_1$ to about $C_{20}$, and

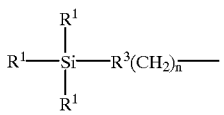

provided at least one $R^2$ is selected from among hydroxide, sulfide, sulfate, carbonate, phosphate, phosphite, phosphonate, sulfonate, mercapto, mercapto alcohol, or mercaptoesters, and carboxylates substituted or unsubstituted of $C_1$ to about $C_{20}$;

$R^3$ is $(CH_2)_m$, aryl or cycloalkyl;

m=0 to 17, n=1 to 18, sum of n plus m=1 to 18 except when $R^3$ is aryl or cycloalkyl, then n=at least 2;
and M—O— is the metal oxide component of the solid support.

4. A solid heterogeneous catalyst for esterification or transesterification reactions or a urethane, urea, silicone, or amino forming reactions comprising an organotin functionalized silane chemically bonded to a solid metal oxide through an oxygen bridge corresponding to the formula:

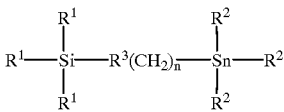

wherein:
each $R^1$ is independently selected from the group consisting of F, Cl, Br, I, OR, M—O—, and R, where R is substituted or unsubstituted $C_1$ to $C_{18}$alkyl, $C_5$ to $C_{12}$ cycloalkyl, or aryl, provided at least one value of $R^1$ is M—O—;
each $R^2$ is independently selected from $R^1$, benzyl, vinyl, allyl, hydride, and

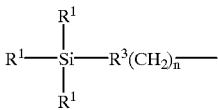

$R^3$ is $(CH_2)_m$, aryl or cycloalkyl;

m=0 to 17, n=1 to 18, sum of n plus m=1 to 18 except when $R^3$ is aryl or cycloalkyl, then n=at least 2; and M—O— is the metal oxide component of the solid support.

5. The catalyst of claim 4 wherein $R^3$ is $(CH_2)_m$ and the sum of n plus m is either 1 or 3 resulting in $R^3(CH_2)_n$— being either a methylene or propylene group.

6. The catalyst of claim 4 wherein at least one of the labile group values F, Cl, Br, I, or OR for $R^2$ has been replaced with a catalytically active group selected from the group consisting of oxide, hydroxide, sulfide, sulfate, carbonate, phosphate, phosphite, phosphonate, sulfonate, mercapto, mercapto alcohol, or mercaptoesters, and carboxylates substituted or unsubstituted of $C_1$ to about $C_{20}$.

7. The catalyst of claim 5 wherein at least one of the labile group values F, Cl, Br, I, or OR for $R^2$ has been replaced with a catalytically active group selected from the group consisting of oxide, hydroxide, sulfide, sulfate, carbonate, phosphate, phosphite, phosphonate, sulfonate, mercapto, mercapto alcohol, or mercaptoesters, and carboxylates substituted or unsubstituted of $C_1$ to about $C_{20}$.

8. A heterogeneous catalyst for esterification or transesterification reactions or a urethane, urea, silicone, or amino forming reactions comprising the composition of claim 5 wherein at least one of the labile group values F, Cl, Br, I, or OR for $R^2$ has been replaced with a catalytically active group selected from the group consisting of oxide, hydroxide, sulfide, sulfate, carbonate, phosphate, phosphite, phosphonate, sulfonate, mercapto, mercapto alcohol, or mercaptoesters, and carboxylates substituted or unsubstituted of $C_1$ to about $C_{20}$.

9. The composition of claim 1 wherein said metal oxide support is selected from the group consisting of glass, mica, silica gel, alumina, aluminasiloxane, kaolin, titania, zirconia and chromium oxide.

10. The composition of claim 2 wherein said metal oxide support is selected from the group consisting of glass, mica, silica gel, alumina, aluminasiloxane, kaolin, titania, zirconia and chromium oxide.

* * * * *